United States Patent [19]

Larkin

[11] Patent Number: 4,816,460

[45] Date of Patent: Mar. 28, 1989

[54] INSECTICIDAL DIOXOPYRIMIDINE CARBOXYANIDES

[75] Inventor: John P. Larkin, Berkhamsted, England

[73] Assignee: Burroughs Wellcome Co., Research Triangle Park, N.C.

[21] Appl. No.: 939,547

[22] Filed: Dec. 9, 1986

[30] Foreign Application Priority Data

Dec. 24, 1985 [GB] United Kingdom ............... 8531815

[51] Int. Cl.$^4$ .................. A61K 31/515; C07D 401/12
[52] U.S. Cl. ................................ 514/270; 544/299; 544/301; 544/302
[58] Field of Search ............... 544/299, 301, 302; 514/270

[56] References Cited

U.S. PATENT DOCUMENTS

| | | | |
|---|---|---|---|
| 3,961,061 | 6/1976 | Krämer et al. | 544/301 |
| 4,239,762 | 12/1980 | Krämer et al. | 544/300 |
| 4,283,444 | 8/1981 | de Sousa et al. | 544/301 |
| 4,602,912 | 7/1986 | de Sousa et al. | 544/300 |
| 4,670,441 | 7/1987 | Kühne et al. | 544/300 |

FOREIGN PATENT DOCUMENTS

| | | |
|---|---|---|
| 102327 | 3/1984 | European Pat. Off. . |
| 105029 | 4/1984 | European Pat. Off. ............ 544/301 |
| 135155 | 3/1985 | European Pat. Off. . |
| 167491 | 1/1986 | European Pat. Off. . |
| 2405732 | 8/1975 | Fed. Rep. of Germany . |
| 2936457 | 3/1980 | Fed. Rep. of Germany . |
| 2163423 | 2/1986 | United Kingdom . |

OTHER PUBLICATIONS

Derwent Abstract 85–160403/27.
Derwent Abstract 57313w.
Derwent Abstract 55631w/34.
Derwent Abstract 27871k/12.
Derwent Abstract 22353c/13.
Derwent Abstract 85–070341/12.
Derwent Abstract 84–090429/15.
Derwent Abstract 84–090428/15.
Derwent Abstract 84–064292/11.
Derwent Abstract 09552c/06.
Derwent Abstract 79372y/45.
Derwent Abstract 93363x/50.
Derwent Abstract 86–009403/02.
Derwent Abstract 86–048610/08.
Derwent Abstract 86–022827/04.
De Sousa et al., CA101–72748b (1984).
De Sousa et al., CA 101–19102k (1984).
Burckhardt et al., CA 103–178271x (1985).
Kuehne et al., CA 105–60628g (1986).

*Primary Examiner*—Donald G. Daus
*Assistant Examiner*—Cecilia Shen
*Attorney, Agent, or Firm*—Donald Brown

[57] ABSTRACT

1,3-Dimethyl-4,6-dioxo-2-thioxo-N-[4-(4'trifluoromethylphenoxy)phenyl] perhydropyrimidine-5-carboxamide and analogues are useful pesticides, particularly against insect pests of timber.

3 Claims, No Drawings

INSECTICIDAL DIOXOPYRIMIDINE CARBOXYANIDES

The present invention relates to novel chemical compounds having pesticidal activity, to methods for their preparation, to compositions containing them and to their use in the control of pests. More particularly the invention relates to a class of dioxopyrimidine carboxamides.

DE-A-2 405 732 (Bayer) discloses as endo- and ectoparasiticides certain thiobarbituric acid derivatives, including amides thereof, but none having an aryloxyaryl group attached to the amide nitrogen.

In a first aspect, the present invention provides a compound of Formula (I):

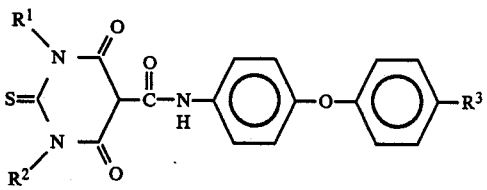

or a salt thereof, wherein $R^1$ and $R^2$ are the same or different and each is $C_{1-4}$ alkyl and $R^3$ is chlorine, bromine or trifluoromethyl.

It will be appreciated that compounds of Formula (I) exist as keto-enol tautomers; both forms, and mixtures thereof, are within the scope of the invention.

Those compounds of Formula (I) wherein $R^1$ and $R^2$ are methyl are preferred. $R^3$ is preferably trifluoromethyl. 1,3-Dimethyl-4,6-dioxo-2-thioxo-N-[4-(4'-trifluoromethylphenoxy)phenyl]perhydropyrimidine-5-carboxamide is a preferred compound of the present invention. According to an alternative nomenclature, this compound may be named as 1,3-dimethyl-5-[4-(4'-trifluoromethylphenoxy)phenylcarbamoyl]-2-thiobarbiturate.

The compounds of Formula (I) may form salts with a suitable base, for example with the alkali metal elements, such as sodium or potassium or with trialkylamines, for example with triethylamine. The compounds of Formula (I), and their salts with suitable bases, are believed to have useful pesticidal activity, and, in particular are believed to have activity against grain, cloth, flour and wood pests. 1,3-Dimethyl-4,6-dioxo-2-thioxo-N-[4-(4'-trifluoromethyl-phenoxy)phenyl]perhydropyrimidine-5-carboxamide has been found to have good activity against the flour beetle *Stegobium paniceum* which is also indicative of activity against wood beetles of the genus Anobium, for example *Anobium punctatum*.

The compounds of Formula (I) may be prepared by
(a) reaction of a compound of Formula (II) with a compound of Formula (III):

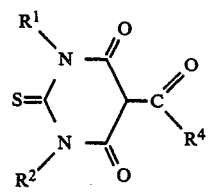

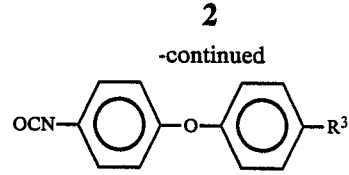

(b) by reaction of a compound of Formula (IV) with a compound of Formula (V):

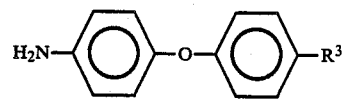

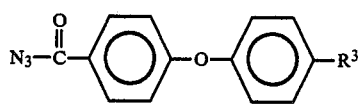

where $R^4$ is halo, alkoxy or phenoxy optionally substituted by nitro;

(c) by reaction of a compound of Formula (II) above with a compound of Formula (VI):

Reactions (a) and (c) are normally carried out in the presence of a base, suitably an amine such as triethylamine, in an inert solvent, for example a hydrocarbon such as benzene or toluene, at an elevated temperature, for example between 40° and 200° C., preferably 70° to 150° C.; and conveniently under reflux.

Step (b) is normally carried out at between 50° and 230° C., preferably 70° to 190° C., at atmospheric or increased pressure.

The compound of Formula (III) may be prepared from the corresponding amine by reaction with phosgene in an inert solvent, for example a hydrocarbon such as benzene or toluene at an elevated temperature, for example between 40° and 150° C. and conveniently under reflux.

The amine may be prepared by the reaction of 4-aminophenol with a compound:

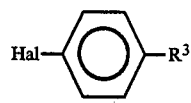

where Hal is a halogen, conveniently chlorine. This reaction is conveniently carried out in a dipolar aprotic solvent, such as DMF or DMSO, in the presence of a base such as sodium hydroxide at an elevated temperature, for example between 50° and 200° C. and conveniently under reflux.

The compounds of Formula (I) may be used to control arthropods such as insects and acarines.

The compounds of Formula (I) may be used for such purposes by application of the compounds themselves or in diluted form in known fashion as a dip, spray, lacquer, foam, dust, powder, aqueous suspension, paste, gel, shampoo, grease, combustible solid, vapourising mat, wettable powder, granule, aerosol, emulsifiable concentrate, oil suspensions, oil solutions, pressure-pack, impregnated article or pour-on formulation. Dip concentrates are not applied per se, but diluted with water and the animals immersed in a dipping bath containing the dip wash. Sprays may be applied by hand or by means of a spray race or arch. The animal, plant or surface may be saturated with the spray by means of high volume application or superficially coated with the spray by means of light or ultra low volume application. Aqueous suspensions may be applied in the same manner as sprays or dips. Dusts may be distributed by means of a powder applicator or, in the case of animals, incorporated in perforated bags attached to trees or rubbing bars. Pastes, shampoos and greases may be applied manually or distributed over the surface of an inert material against which animals rub and transfer the material to their skins. Pour-on formulations are dispensed as a unit of liquid of small volume on to the backs of animals such that all or most of the liquid is retained on the animals.

The compounds of Formula (I) may be formulated either as formulations ready for use on the animals plants or surface or as formulations requiring dilution prior to application, but both types of formulation comprise a compound of Formula (I) in intimate admixture with one or more carriers or diluents. The carriers may be liquid, solid or gaseous or comprise mixtures of such substances, and the compound of Formula (I) may be present in a concentration of from 0.025 to 99% w/v depending upon whether the formulation requires further dilution.

Dusts, powder and granules comprise the compound of Formula (I) in intimate mixture with a powdered solid inert carrier for example suitable clays, kaolin, talc, mica, chalk, gypsum, vegetable carriers, starch and diatomaceous earths.

Sprays of a compound of Formula (I) may comprise a solution in an organic solvent (e.g. those listed below) or an emulsion in water (dip wash or spray wash) prepared in the field from an emulsifiable concentrate (otherwise known as a water miscible oil), which may also be used for dipping purposes. The concentrate preferably comprises a mixture of the active ingredient, with or without an organic solvent and one or more emulsifiers. Solvents may be present within wide limits but preferably in an amount of from 0 to 90% w/v of the composition and may be selected from kerosene, ketones, alcohols, xylene, aromatic naphtha, and other solvents known in the formulating art. The concentration of emulsifiers may be varied within wide limits but is preferably in the range of 5 to 25% w/v and the emulsifiers are conveniently non-ionic surface active agents including polyoxyalkylene esters of alkyl phenols and polyoxyethylene derivatives of hexitol anhydrides and anionic surface active agents including Na lauryl sulphate, fatty alcohol ether sulphates, Na and Ca salts of alkyl aryl sulphonates and alkyl sulphosuccinates.

Wettable powders comprise an inert solid carrier, one or more surface active agents, and optionally stabilisers and/or anti-oxidants.

Emulsifiable concentrates comprise emulsifying agents, and often an organic solvent, such as kerosene, ketones, alcohols, xylenes, aromatic naphtha, and other solvents known in the art.

Wettable powders and emulsifiable concentrates will normally contain from 5 to 95% by weight of the active ingredient, and are diluted, for example with water, before use.

Lacquers comprise a solution of the active ingredient in an organic solvent together with a resin, and optionally a plasticiser.

Dip washes may be prepared not only from emulsifiable concentrates but also from wettable powders, soap based dips and aqueous suspensions comprising a compound of Formula (I) in intimate admixture with a dispersing agent and one or more surface active agents.

Aqueous suspensions of a compound of Formula (I) may comprise a suspension in water together with suspending, stabilizing or other agents. The suspensions or solutions may be applied per se or in a diluted form in known fashion.

Greases (or ointments) may be prepared from vegetable oils, synthetic esters of fatty acids or wool fat together with an inert base such as soft paraffin. A compound of Formula (I) is preferably distributed uniformly through the mixture in solution or suspension. Greases may also be made from emulsifiable concentrates by diluting them with an ointment base.

Pastes and shampoos are also semi-solid preparations in which a compound of Formula (I) may be present as a uniform dispersion in a suitable base such as soft or liquid paraffin or made on a non-greasy basis with glycerin, mucilage or a suitable soap. As greases, shampoos and pastes are usually applied without further dilution they should contain the appropriate percentage of the compound of Formula (I) required for treatment.

Aerosol sprays may be prepared as a simple solution of the active ingredient in the aerosol propellant and co-solvent such as halogenated alkanes and the solvents referred to above, respectively. Pour-on formulations may be made as a solution or suspension of a compound of Formula (I) in a liquid medium. An avian or mammal host may also be protected against infestation of acarine ectoparasites by means of carrying a suitably-moulded, shaped plastics article impregnated with a compound of Formula (I). Such articles include impregnated collars, tags, bands, sheets and strips suitably attached to appropriate parts of the body.

The concentration of the compound of Formula (I) to be applied to an animal will vary according to the compound chosen, the interval between treatments, the nature of the formulation and the likely infestation, but in general 0.001 to 20.0% w/v and preferably 0.01 to 10% of the compound should be present in the applied formulation. The amount of the compound deposited on an animal will vary according to the method of application, size of the animal, concentration of the compound in the applied formulation, factor by which the formulation is diluted and the nature of the formulation by in general will lie on the range of from 0.0001% to 0.5% except for undiluted formulations such as pour-on formulations which in general will be deposited at a concentration in the range from 0.1 to 20.0% and preferably 0.1 to 10%.

The compounds of Formula (I) are also of use in the protection and treatment of plant species, in which case an effective insecticidal or acaricidal amount of the active ingredient is applied. The application rate will vary according to the compound chosen, the nature of the formulation, the mode of application, the plant species, the planting density and likely infestation and other like factors but in general, a suitable use rate for agricultural crops is in the range 0.001 to 3 Kg/Ha and preferably between 0.01 and 1 Kg/HA. Typical formulations for agricultural use contain between 0.0001% and 50% of a compound of Formula (I) and conveniently between 0.1 and 15% by weight of a compound of the Formula (I).

Particular crops include cotton, wheat, maize, rice, sorghum, soya, vines, tomatoes, potatoes, fruit trees and spruce.

Dusts, greases, pastes and aerosol formulations are usually applied in a random fashion as described above and concentrations of 0.001 to 20% w/v of a compound of Formula (I) in the applied formulation may be used.

Compounds of Formula (I) may be applied to timber by immersion of the timber in a solution of the compound, by spraying or by pressure impregnation. The compounds may be mixed with other insecticides and/or fungicides. The timber may be freshly sawn, or present in a structure such as a building, ship or piling or it may be formed as an article, for example a telegraph pole or item of furniture.

The compounds of Formula (I) have been found to have activity against the common housefly (*Musca domestica*). In addition, certain compounds of Formula (I) have activity against other arthropod pests including *Tetranychus urticae, Plutella xylostella*, Culex spp. and *Blattella germanica*. The compound of Formula (I) are thus useful in the control of arthropods e.g. insects and acarines in any environment where these constitute pests, e.g. in agriculture, in animal husbandry, in public health control, timber and in domestic situations.

Insect pests include members of the orders Coleoptera (e.g. Anobium, Tribolium, Sitophilus, Diabrotica, Anthonomus or Anthrenus spp.), Lepidoptera (e.g. Ephestia, Plutella, Chilo, Heliothis, Spodoptera, Tinea or Tineola spp.), Diptera (e.g. Musca, Aedes, Culex, Glossina, Stomoxys, Haematobia, Tabanus, Hydrotaea, Lucilia, Chrysomia, Callitroga, Dermatobia, Hypoderma, Liriomyza, and Melophagus spp.) Phthiraptera, Malophaga e.g. Damalinia spp. and Anoplura e.g. Linognathus and Haematopinus spp.), Hemiptera (e.g. Aphis, Bemisia, Aleurodes, Nilopavata, Nephrotetix or Cimex spp.), Orthoptera (e.g. Schistocerca or Acheta spp.), Dictyoptera (e.g. Blattella, Periplaneta or Blatta spp.), Hymenoptera (e.g. Solenopsis or Monomorium spp.), Isoptera (e.g. Reticulitermes spp.), Siphonaptera (e.g. Ctenocephalides or Pulex spp.), Thysanura (e.g. Lepisma spp.), Dermaptera (e.g. Forficula spp.) and Psocoptera (e.g. Peripsocus spp.).

Acarine pests include ticks, e.g. members of the genera Boophilus, Rhipicephalus, Amblyomma, Hyalomma, Ixodes, Haemaphysalis, Dermocentor and Anocentor, and mites and manges such as Tetranychus, Psoroptes, Psorergates, Chorioptes, Demodex spp.

Compounds of the invention may be combined with one or more other active ingredients (for example pyrethroids, carbamates and organophosphates) and/or with attractants and the like. Furthermore, it has been found that the activity of the compounds of the invention may be enhanced by the addition of a synergist or potentiator, for example: one of the oxidase inhibitor class of synergists, such as piperonyl butoxide or NIA 16388; a second compound of the invention; or a pyrethroid pesticidal compound. When an oxidase inhibitor synergist is present in a formula of the invention, the ratio of synergist to compound of Formula (I) will be in the range 25:1–1:25 eg about 10:1.

Stabilisers for preventing any chemical degradation which may occur with the compounds of the invention include, for example, antioxidants (such as tocopherols, butylhydroxyanisole and butylhydroxytoluene) and scavengers (such as epichlorhydrin).

It will be undeerstood that what we will claim may comprise:

(a) compounds of Formula (I);
(b) processes for the preparation of compounds of Formula (I);
(c) insecticidal and acaricidal compositions comprising a compound of Formula (I) in admixture with a carrier;
(d) processes for the preparation of such pesticidal compositions;
(e) methods for the control of insect or acarine pests comprising the application to the pest or its environment of a compound of Formula (I);
(f) synergised pesticidal compositions comprising a compound of Formula (I); and
(g) potentiating or non-potentiating mixtures of a compound of Formula (I) and another pesticidal compound;
(h) novel intermedates in the preparation of compounds of Formula (I).

The following Examples illustrate, in a non-limiting manner, preferred aspects of the invention. All temperatures are in degrees Celsius.

EXAMPLE 1

1,3-Dimethyl-4,6-dioxo-2-thioxo-N-[4-(4-trifluoromethylphenoxy)phenyl]perhydropyrimidine-5-carboxamide A solution of potassium hydroxide (10.8 g.) in water (10 ml) was added to a solution of 4-aminophenyl (17 g.) in dimethylsulphoxide (120 ml). The volume of the reaction mixture was reduced to about 40 ml by distillation in vacuo (20 mm.). The reaction mixture was cooled. 4-Chlorobenzotrifluoride (20.6 ml) was added and the mixture was heated at 120° for 3 hours. After cooling the mixture was poured into water. The aqueous mixture was extracted with diethyl ether. The ether extracts were washed with water, dried over anhydrous magnesium sulphate and evaporated in vacuo. The resulting solid was washed with hexane.

4-Amino-4'-trifluomethyldiphenyl ether was obtained as a brown solid (10.0 g.) (melting point 75°–76°).

Mass spectrum (MS), chemical ionisation: M+1, 254.

4-Amino-4'-trifluoromethyldiphenyl ether (15 g.) was added in small portions to a stirred solution of phosgene in toluene (180 ml, 12.5% solution) at 0°. The mixture was refluxed, with stirring, for 3 hours. The solvent was removed in vacuo. Distillation gave 4-(4'-trifluoromethyl-phenoxy)phenylisocyanate as a pale yellow oil (8.1 g, boiling point 110°–114°, 0.5 mm).

4-(4'-Trifluoromethylphenoxy)phenyl isocyanate (3.7 g.) was added to a stirred mixture of 1,3-dimethyl-2-thiobarbituric acid (2.3 g.) and triethylamine (1.7 ml.) in dry benzene (30 ml.). The mixture was refluxed for 12 hours. The mixture was evaporated in vacuo. Diethyl ether (10 ml.) was added to the gummy residue and the mixture was acidified with 1N hydrochloric acid. The mixture was filtered and the solid was washed with water and then ethanol.

1,3-Dimethyl-4,6-dioxo-2-thioxo-N-[4-(4'-trifluoromethyl phenoxy)phenyl]perhydropyrimidine-5-carboxamide was obtained as an off-white solid (melting point 155°).

Nuclear magnetic resonance spectrum (NMR) was as follows:

$^1$H[ppm from TMS in CDCl$_3$ (containing 5% triethylamine), integral, number of peaks]: 7.80–7.40, 4H, m; 7.20–6.80, 4H, m; 3.60, 6H, S.

Mass spectrum (MS), chemical ionisation: M+1, 452.

EXAMPLE 2

1,3-Dimethyl-4,6-dioxo-2-thioxo-N-[4-(4'-chlorophenoxy)phenyl]perhydro-pyrimidine-5-carboxamide This made by a method analogous to that of Example 1, but starting from 4-amino-4'-chlorodiphenylether (Beilstein, 13 II 227).

White solid, m.p. 141° C. Mass spectrum (chemical ionisation) M+1 418. NMR (Solvent (CD$_3$)$_2$SO+triethylamine): 7.5, 2H, d, 7; 7.35, 2H, d, 7; 6.90, 4H, m; 3.60, 6H, s.

EXAMPLE A

Activity of compound of Example 1 against Stegobium 5 ml of test solution in acetone (Analar) was pipetted onto 50 g wholemeal flour (Dove Farm), left to dry, then placed into ointment pots. The flour was infested with ca. 20 *Stegobium paniceum* adults. The test was left until the progeny of these adults had emerged from the control treatments. The progeny were counted and scored as follows:

$$\text{percent reduction} = \frac{(\text{No. in control}) - (\text{No. in treatment})}{(\text{No. in control})} \times 100$$

RESULTS

| COMPOUND | RATE (PPM) | PERCENT REDUCTION | COMMENT |
|---|---|---|---|
| of Example 1 | 2 | 87 | Mainly Dead |
|  | 10 | 93 | Mainly Dead |
|  | 50 | 94 | Mainly Dead |

COMPARATIVE EXAMPLES 1,3-Dimethyl-4,6-dioxo-2-thioxo-N-(3,4-dichlorophenyl) perhydro-pyrimidine-5-carboxamide (DE-A-2 405 732, page 20, third compound) gave only 8% reduction at 50 ppm in the test of Example A above.

I claim:

1. A method of combatting an insect pest by applying to the pest or its environment a composition comprising an effective insecticidal amount of a compound of the formula

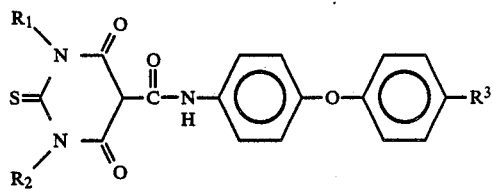

and a carrier or a salt thereof, wherein R$^1$ and R$^2$ are the same or different and are C$_{1-4}$ alkyl, and R$^3$ is chlorine, bromine or trifluoromethyl.

2. A method according to claim 1 wherein the compound is 1,3-dimethyl-4,6-dioxo-2-thioxo-N-[4'-trifluoromethylphenoxy)phenyl]perhydropyrimidine-5-carboxamide.

3. A method according to claim 1 wherein the pest is an insect pest of timber.

* * * * *